US009122670B2

(12) United States Patent
Chabanas et al.

(10) Patent No.: US 9,122,670 B2
(45) Date of Patent: Sep. 1, 2015

(54) METHOD FOR DETERMINING ARTICULAR BONE DEFORMITY RESECTION USING MOTION PATTERNS (75) Inventors: Laurence Chabanas, Saint-Pierre-d'Allevard (FR); Stéphane Lavallee, Saint-Martin-d'Uriage (FR); Jerome Tonetti, Grenoble (FR); Thomas Byrd, Nashville, TN (US); Bryan Talmadge Kelly, Riverside, CT (US); Christopher Larson, Edina, MN (US)

(73) Assignee: A2 Surgical, Le Mans (FR)

( * ) Notice: Subject to any disclaimer, the term of this patent is extended or adjusted under 35 U.S.C. 154(b) by 240 days.

(21) Appl. No.: 13/704,063

(22) PCT Filed: Jun. 16, 2011

(86) PCT No.: PCT/IB2011/001686
§ 371 (c)(1),
(2), (4) Date: Dec. 13, 2012

(87) PCT Pub. No.: WO2011/158116
PCT Pub. Date: Dec. 22, 2011

(65) Prior Publication Data
US 2013/0085723 A1    Apr. 4, 2013

Related U.S. Application Data (60) Provisional application No. 61/355,209, filed on Jun. 16, 2010.

(51) Int. Cl.
G06F 17/50    (2006.01)
G06F 19/26    (2011.01)
G06T 17/00    (2006.01)
G06T 19/20    (2011.01)

(52) U.S. Cl.
CPC .............. *G06F 19/26* (2013.01); *G06T 17/00* (2013.01); *G06T 19/20* (2013.01); *G06T 2210/21* (2013.01); *G06T 2210/41* (2013.01); *G06T 2219/2021* (2013.01)

(58) Field of Classification Search
CPC ......... G06F 19/26; G06T 17/00; G06T 19/20; G06T 19/26; G06T 2210/41; G06T 2210/21
USPC .................................................. 703/1; 382/128
See application file for complete search history.

(56) References Cited

U.S. PATENT DOCUMENTS

| 5,995,738 | A | 11/1999 | DiGioia et al. |
| 7,672,709 | B2 | 3/2010 | Lavallee et al. |
| 2005/0143676 | A1 | 6/2005 | De Guise et al. |
| 2007/0122233 | A1 | 5/2007 | Maier et al. |
| 2007/0195933 | A1 | 8/2007 | Bogojevic et al. |
| 2008/0086150 | A1 | 4/2008 | Mathis et al. |
| 2008/0177173 | A1 | 7/2008 | Deffenbaugh et al. |
| 2008/0214960 | A1 | 9/2008 | Hodgson et al. |
| 2008/0312663 | A1* | 12/2008 | Haimerl et al. ............... 606/130 |
| 2008/0319449 | A1 | 12/2008 | Tuma et al. |
| 2009/0017430 | A1 | 1/2009 | Muller-Daniels et al. |
| 2009/0089034 | A1 | 4/2009 | Penney et al. |
| 2009/0112214 | A1 | 4/2009 | Philippon et al. |
| 2009/0285465 | A1* | 11/2009 | Haimerl et al. ............... 382/131 |
| 2010/0049493 | A1 | 2/2010 | Haimerl |
| 2011/0029116 | A1* | 2/2011 | Jordan et al. ................... 700/98 |

FOREIGN PATENT DOCUMENTS

JP    2009273521    11/2009

OTHER PUBLICATIONS

Dudda M. et al, "Do Normal Radiographs Exclude Asphericity of the Femoral Head-Neck Junction?", Clin Orthop Relat Res (2009) 467:651-659.

Rakhra K.S. et al, "Comparison of MRI Alpha Angle Measurement Planes in Femoroacetabular Inpingement", Clin Orthop Relat Res (2009) 647:660-665.

Kang et al, "Accurate simulation of hip joint range of motion", Computer Animation Conference—CA, pp. 215-219, 2002.

Brunner A. et al, "Evaluation of a Computer Tomography-Based Navigation System Prototype for Hip Arthroscopy in the Treatment of Femoroacetabular Cam Impingement", Arthroscopy: The Journal of Arthroscopic and Related Surgery, vol. 25, No. 4 Apr. 2009: pp. 382-391.

Arbabi E. et al, "A fast method for finding maximum range of motion in the hip joint", CAOS 2007, Heidelberg, Germany, p. 20-23.
Arbabi E. et al, "Penetration Depth Method—Novel Real-Time Strategy for Evaluating Femoroacetabular Impingement", Journal of Orthopaedic Research, vol. 28, Issue 7, pp. 880-886, Jul. 2010.
Dario P. et al, "A Novel Mechatronic Tool for Computer-Assisted Arthroscopy", IEEE Engineering in Medicine and Biology Society 2000;4(1):15-29.
Hodgson A.J. et al, "Computer-assisted femoral head resurfacing", Computer Aided Surgery, Sep./Nov. 2005; 10(5/6): 337-343.
Kendoff D. et al, "Feasibility of a navigated registration technique in FAI surgery", Archives of Orthopaedic and Trauma Surgery, vol. 131, No. 2, pp. 167-172, 2011.
Wengert C. et al, "Markerless Endoscopic Registration and Referencing", Med Image Comput Comput Assist Interv. 2006;9(pt 1):816-23.
Monahan E. et al, "Computer-aided navigation for arthroscopic hip surgery using encoder linkages for position tracking", Int J Med Robotics Comput Assist Surg 2006; 2: 271-278.
Monahan E. et al, "A study of user performance employing a computer-aided navigation system for arthroscopic hip surgery", Int J CARS (2007) 2:245-252.
Charbonnier C. et al, "Motion study of the hip joint in extreme postures", The Visual Computer, vol. 25, No. 9, pp. 873-882, 2009.
Gilles B. et al, "MRI-based Assessment of Hip Joint Translations", J Biomech, vol. 42, Jun. 2009.
Murphy S.B. et al, "Arthroscopic percutaneous computer assisted FAI relief using a new method of CT-fluoro registration", Computer-Assisted Orthopedic Surgery—International, 2007.
Barrett A.R.W et al, "Preoperative planning and intraoperative guidance for accurate computer-assisted minimally invasive hip resurfacing surgery", Proc. IMechE vol. 220 Part H, 2006.
Puls M. et al, "Simulation of Hip Motion for Impingement Detection: A Comparison of Four Strategies", Journal of Biomechanics 41(S1), 16th ESB Congress, Oral Presentations, Tuesady Jul. 8, 2008.
Cai D. et al, "Rapid Impingement Detection System with Uniform Sampling for Ball-and-Socket Joint", Workshop on 3D Physiological Human, Zermatt, Switzerland, Dec. 1-2, 2008.
Tannast M. et al, << Computer-assisted Simulation of Femoroacetabular Impingement Surgery >>, In JB Stiehl, WH Konerman, RG Haaker, AM DiGioia (eds.): "Navigation and MIS in Orthopaedic Surgery", Berlin, Heidelberg, New York: Springer-Verlag. pp. 448-455, 2006.
Tannast M. et al, "Noninvasive three-dimensional assessment of femoroacetabular impingement",Journal of Orthopedic Research, Jan. 2007.
Wu C., "3D Reconstruction and Tracking of Anatomical Structures from Endoscopic Images", Thesis, 2009.
Charbonnier C. et al, "Virtual Hip Joint: from Computer Graphics to Computer-Assisted Diagnosis", Eurographics 2009, Mar. 30-Apr. 3, Munich, Germany.
Kubiak-Langer M et al: "Range of Motion in Anterior Femoroacetabular Impingement", Clinical Orthopaedics and Related Research, vol. 458, May 2007, pp. 117-124, XP55046680, section "Materials and Methods".
Qingmao Hu et al: "A Fast Impingement Detection Algorithm for Computer-Aided Orthopedic Surgery", Computer Aided Surgery, vol. 6, No. 2, Jul. 30, 2001, pp. 104-110, XP55046688, the whole document.
International Search Report for International Application No. PCT/IB2011/001686, mailed Dec. 11, 2012.
Patent Examination Report No. 1 for Australian Patent Application No. 2011266699 dated May 5, 2014, 3 pages.
Official Inquiry and English Translation for Japanese Patent Application No. 2013-514801 dated Mar. 16, 2015, 5 pages.
Kubiak-Langer M. et al, "Range of Motion in Anterior Femoroacetabular Impingement", Clinical Orthopaedics and Related Research, No. 458, pp. 117-124.
Zaraogza E-J., "3D CT and the Imaging Approach to Femoroacetabular Impingement Syndrome", Section 4, Orthopedic Imaging, pp. 143-150.

* cited by examiner

*Primary Examiner* — Eunhee Kim
(74) *Attorney, Agent, or Firm* — David L. Fox; JL Salazar Law Fim (57) ABSTRACT

The invention relates to a method for real-time determination an optimal corrected surface of a first bone and/or a second bone forming together an articulation, the first and/or second bones presenting an overgrowth deformation, said corrected surface providing a greater range of motion of the articulation, the method comprising the following steps: i) constructing from acquired images of the articulation 3D voxel models of the first bone and the second bone; ii) for each of first and second bone voxel models, constructing a coordinate system defined by a center and three axes; iii) applying a motion pattern on the coordinate system of the second bone with respect to the coordinate system of the first bone, a motion pattern being a set of contiguous positions of the first or second bone coordinate systems with respect to the other bone coordinate system, the contiguous positions defining a movement of one bone with respect to the other, wherein said motion pattern is initially loaded from a data base of predefined motion patterns; iv) determining a resection volume from said motion pattern as being the union of interpenetration volumes of the first or second bone voxel model with the other bone voxel model for each position of the motion pattern; v) determining the optimal corrected surface by virtually removing said resection volume from the first and/or the second bone voxel model.

15 Claims, 10 Drawing Sheets

METHOD FOR DETERMINING ARTICULAR BONE DEFORMITY RESECTION USING MOTION PATTERNS

TECHNICAL FIELD

The invention relates to the field of computer assisted surgery, and more particularly to a method for determining bone resection on a deformed articulation surface.

BACKGROUND OF THE INVENTION

Articulations of the human body are often very complex systems and no precise generic model exists to capture all the variability from one articulation to another. It is therefore necessary to use specific medical images or collection of digital patient data in order to get relevant information to develop techniques, devices and methods that will facilitate a treatment or a diagnosis.

In a specific example related to the hip articulation, structural abnormalities in the morphology of the hip can limit motion and result in repetitive impact of the proximal femoral neck against the acetabular labrum and its adjacent cartilage. Femoro Acetabular Impingement (FAI) is a pathology that can result from a decreased femoral head-neck offset (cam effect), an overgrowth of the bony acetabulum (pincer effect), excessive acetabular retroversion or excessive femoral anteversion, or a combination of these deformities. The cam impingement is generally characterized by a bone overgrowth located at the antero-superior aspect of the femur head-neck junction, which destructures the spherical shape of the femur head. The pincer impingement is generally characterized by an overcoverage located at the anterior aspect of the acetabulum rim. However, the correct and full diagnosis of this pathology is not easy to determine, especially when dealing with subtle deformities. Standard radiographic X-rays are used for the initial diagnosis and then three dimensional (3D) Computed Tomography (CT) scans or Magnetic Resonance Imaging (MRI) exams are generally performed in case of suspected FAI pathology. The processing of the 3D images remains a laborious manual task which cannot ensure accuracy and reproducibility, potentially misleading the diagnosis or the surgical indication. Moreover, even though 3D information can be extracted from such exams, the reconstructed bone volumes remain static and cannot predict with reliability the exact location of the impingement which occurs during the mobilization of the hip.

The surgical treatment of FAI aims at restoring a normal spherical shape to the femur head neck junction at the level of the bony cam lesion and restoring a normal coverage rate of the acetabular rim at the level of the pincer lesion, by removing the excess of bone. The result of this bony reshaping is the restoration of a greater range of motion of the hip, without impingement. Conventionally, the open surgical approach had initially been adopted since it provides a full exposure of the bone and direct access to the anatomy to be treated. Though, since minimally invasive procedures have grown in popularity by reducing the pain, morbidity and recovery time for patient, arthroscopic treatment of FAI has been explored in the last decade, which requires the use of an endoscopic camera and specific small instruments that can pass through various types of canulas. Advantages include minimally invasive access to the hip joint, peripheral compartments, and associated soft tissues. Furthermore, arthroscopy allows for a dynamic, intra-operative assessment and correction of the offending lesions. However, due to the depth of the joint and the reduced visibility and access, theses hip arthroscopy procedures are difficult to perform and not all surgeons feel comfortable about adopting the technique. The success of such arthroscopic interventions relies on correct diagnosis, accurate pre-operative assessment of the pathology, very meticulous intra-operative evaluation and a thorough and accurate correction of impingement lesions on both the femoral and acetabular sides, which can only be accomplished after a laborious learning curve over many cases. Failure of arthroscopic procedures for FAI is most commonly associated with incomplete decompression of the bony lesions.

Hence, one important issue is the difficulty to determine precisely and in a reproducible manner the location and amount of bone to be resected on a deformed articulation bone surface in order to recreate a smooth bone surface. The surgeons are generally applying 2D templates over the patient X-ray images to try to estimate the resection to be achieved. This remains a very limited and inaccurate method for addressing a problem in 3D space. The acquisition of a pre-operative 3D image of the patient is becoming a common protocol in these pathologies, thus increasing the level of information of the surgeon on the pathological problem. However, there are very few tools to process these 3D images and use resulting information in order to provide a proposition for the bone correction to be performed. Most of the imaging systems used to acquire the 3D images provide 3D reconstruction of bone surface models, however, the processing have to be applied manually and the results are only static projection views of the bone models. There exists some software proposing to simulate the resection pre-operatively, like the Mimics® software from Materialise, Leuven, Belgium, but the tools they offer are only simulation of bone milling process to be applied manually by the user, which takes a lot of time to perform, and does not guarantee reproducible results based on objective criteria. Another method consists in using the opposite side of the patient and mirror the opposite surface to define an optimal correction surface on the deformed side, but accurate results cannot be provided if the opposite side has also some early stage of deformity.

SUMMARY OF THE INVENTION

The invention provides a method for real-time determination an optimal corrected surface of a first bone and/or a second bone forming together an articulation, the first and/or second bones presenting an overgrowth deformation, said corrected surface providing a greater range of motion of the articulation, the method comprising the following steps:
  i) constructing from acquired images of the articulation 3D voxel models of the first bone and the second bone;
  ii) for each of first and second bone voxel models, constructing a coordinate system defined by a center and three axes;
  iii) applying a motion pattern on the coordinate system of the second bone with respect to the coordinate system of the first bone, a motion pattern being a set of contiguous positions of the first or second bone coordinate systems with respect to the other bone coordinate system, the contiguous positions defining a movement of one bone with respect to the other, wherein said motion pattern is initially loaded from a data base of predefined motion patterns;
  iv) determining a resection volume from said motion pattern as being the union of interpenetration volumes of the first or second bone voxel model with the other bone voxel model for each position of the motion pattern;

v) determining the optimal corrected surface by virtually removing said resection volume from the first and/or the second bone voxel model.

According to an embodiment of the invention, the motion pattern defines a movement of the second bone voxel model with respect to the first bone voxel model, the first bone voxel model being fixed, each position of the second bone voxel model during the movement being defined by three angles of rotation around the axes of the coordinate system of the first bone.

According to another embodiment of the invention, the motion pattern defines a movement of the first bone voxel model with respect to the second bone voxel model, the second bone voxel model being fixed, each position being defined by three angles of rotation around the axes of the coordinate system of the first or second bone.

Each motion pattern of the data base advantageously represents the movement and amplitudes of the articulation corresponding to a specific activity.

According to a particular embodiment of the invention, the articulation is a hip, the first bone is the pelvis presenting an acetabulum rim, and the second bone is the femur, the bone overgrowth being located on the acetabulum rim and/or on the femur.

The articulation may be modeled as a ball-and-socket joint.

The articulation may also be modeled as a ball-and-socket joint with additional residual translations.

According to an embodiment, the resection volume is split into a resection volume of the first bone and a resection volume of the second bone.

The motion pattern may be updated according to the following steps:
 a. Select an initial motion pattern in the data base of motion patterns;
 b. Apply said initial motion pattern to the second bone voxel model and detect the first position that generates interpenetration between the first and the second bone voxel models;
 c. Extend the motion pattern in a given direction from said first position to determine a trajectory that reaches a desired position, and add positions of the trajectory to the updated motion pattern, including at least the desired position.

Said direction may be generated manually by the user with interactive means.

Otherwise, said direction may be generated automatically as the continuation of the trajectory corresponding to the initial pattern.

The method may further comprise the step of generating new positions in the vicinity of said desired position and adding them to the updated motion pattern to generate the final motion pattern.

In particular, said vicinity may be determined as a set of additional positions starting from the desired position and going in the two directions orthogonal to the direction of the trajectory of the motion pattern with small ranges.

According to an embodiment of the invention, the same motion pattern is applied several times for different corrected surfaces of the second bone for selecting an optimal corrected surface of the second bone.

A computer with specialized hardware and software may be used to determine said interpenetration volume between the first and second bones for a given position of the motion pattern, the method comprising the following steps:

a. Apply the position of the motion pattern to transform each voxel element of the second voxel bone model into a transformed voxel element in the coordinate system of the first voxel bone model.
 b. Determine the interpenetration volume as the set of active voxel elements of the first voxel bone model that coincide with an active transformed voxel element of the second voxel bone model.

DESCRIPTION OF THE DRAWINGS

Further aims, features and advantages of the invention will appear in the following detailed description with reference to illustrative and non limitative drawings, among which.

DETAILED DESCRIPTION OF THE INVENTION;

In reference to the drawings, a method for determination of a bone resection of a deformed surface of articulation bone from real-time simulation of movements described by motion patterns will be hereafter described. The method is used for determining an optimal corrected surface of a bone of the articulation using said motion patterns.

In the following description, the method will be described with reference to the hip articulation. Thus, the method will be primarily used for defining a resection of a deformed surface of the pelvis. However, the invention is not limited to the application to the pelvis but can be used for defining a resection of a deformed surface of any bone of any articulation. The person skilled in the art will easily adapt the method of the invention to such articulations.

A computer is used to run a program that implements the algorithms and methods described below, with the capacity of reading or writing files on a disk or internet network, with display to the user, and optional interaction devices such as 2D or 3D mouse. The program can also be run remotely on a web-based system.

A 3D Computed Tomography (CT) or Magnetic Resonance Image (MRI) examination of the patient is performed in order to provide a 3D image using a specific predefined protocol. For example, axial 2D images of the hip can be acquired to construct the 3D image: the axial 2D images are parallel one with the other and are stacked, creating the 3D image. In addition to the conventional 3D image acquisition protocol for the hip, few extra CT or MRI images at the level of the knee and optionally at the level of the anterior superior iliac spines are also acquired.

The automated determination of the range of motion of the hip articulation from 3D surface models built from CT images has been described in the literature by many authors, and software package for detecting impingement between two bone surface models are available, such as Mimics® software from Materialise, Leuven, Belgium. Using such software makes it possible to detect impingement area between two articulated bones. However, the automated determination of an optimal resection area on the pelvis or femur in correlation with methods to define easily an optimal pattern of desired motions is a difficult problem for which no known solution exists. The main difficulty lies in providing a non technician user with a tool that is easy to use, efficient, and based on reliable references in order to establish a strategy for determining an optimal resection area for a given patient. This difficulty combines the problems of definition of desired motions with issues related to fast computation.

Figure 1:
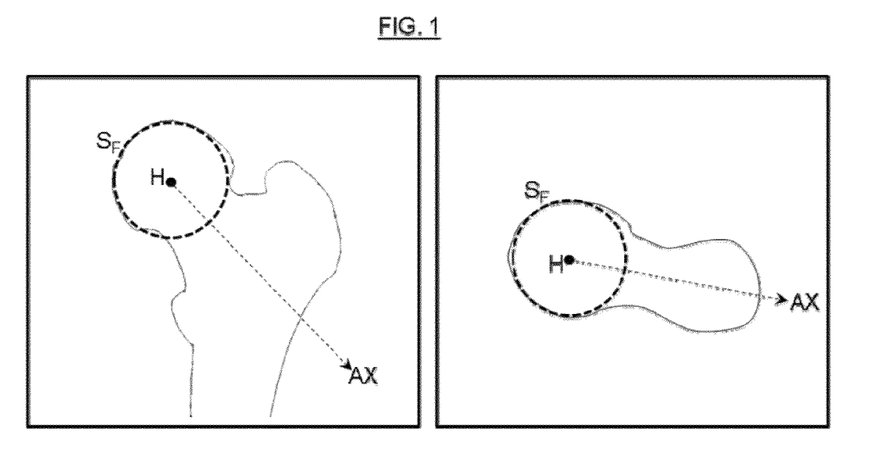
FIG. 1 shows two orthogonal 2D images extracted from the 3D image, in axial and coronal direction, commonly used to determine the position the femoral head sphere and the neck axis.

In a preliminary step the 3D image of the hip is processed for extracting critical geometrical elements characterizing the femur. These geometrical elements can be determined interactively by the user using standard orthogonal 2D images extracted from the 3D image as illustrated in FIG. 1. In the present example, the required geometrical elements are a femoral head sphere SF fitting the non deformed part of the femoral head, a femoral head center point H (center of the sphere SF), a femoral neck axis AX, and a knee center point K.

As illustrated in FIG. 1, the sphere SF is determined by placing interactively a circle on the femur head contours in at least two orthogonal 2D images extracted from the 3D image in axial and coronal directions. The size and position of the femoral head sphere SF is interactively adjusted, which results in the determination of the femoral head sphere SF. The femoral head center H is then determined as the center of the femoral head sphere SF. The neck axis AX is determined by interactively placing a vector line passing through the middle of the femur neck axis in the orthogonal 2D images. The knee center K is determined by interactively placing a point corresponding to the center of the knee in the most distal axial 2D images acquired at the level of the knee (lowest 2D images).

Figure 2:
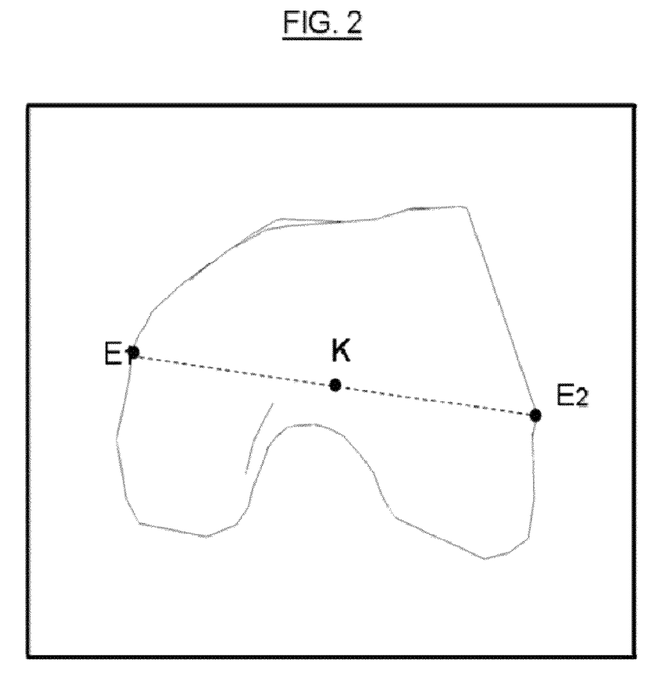
FIG. 2 is a an axial CT 2D image acquired at the level of the knee, commonly used to determine the knee center point.

In a variant embodiment illustrated in FIG. 2, the knee center K is determined by placing interactively two points E1 and E2 corresponding to the epicondyles defined as the most lateral and most medial points of the knee. The knee center K is then determined as the middle of the segment [E1E2].

Specific algorithms can be developed to determine those landmarks automatically.

Figure 3:
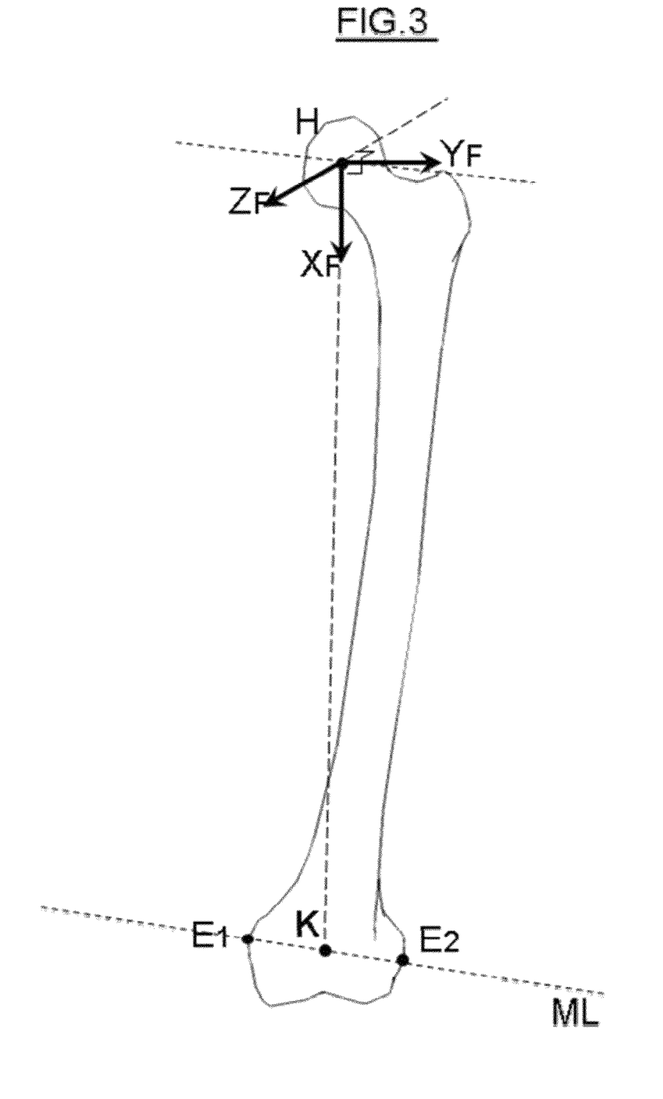
FIG. 3 is a perspective view of a femur, showing the 3D coordinate system determined from femur anatomical landmarks.

From the femoral head center point H, the knee center point K and the axis ML, a femoral coordinate system, defined by an origin and three axes, is determined. The origin of the femoral coordinate system is centered on the femoral head center point H, the $X_F$ axis is defined by the direction of the HK segment, the $Z_F$ axis is defined as the normalized vector product of $X_F$ by ML axis direction vector, the $Y_F$ axis is defined as the vector product of $Z_F$ by $X_F$ to build an orthogonal coordinate system, as illustrated in FIG. 3

On the acetabulum side, the geometrical elements required are an acetabulum center point A, a pair of anterior superior iliac spine crest points $ASIS_L$ and $ASIS_R$, and a pubic symphysis point S.

Figure 4:
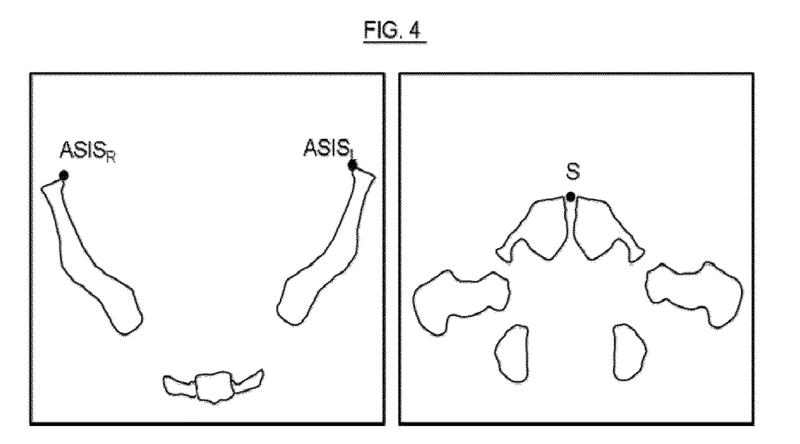
FIG. 4 shows two axial CT 2D images acquired at the level of the iliac spines and in the standard hip acquisition protocol, commonly used to determine the position the anterior superior iliac spines and the pubic symphysis.

In a preferred embodiment of the invention illustrated in FIG. 4, the method for identifying the two pelvic points $ASIS_L$ and $ASIS_R$ comprises determining the two most anterior left and right points in the native 2D images acquired at the level of the iliac spines (highest 2D images). Similarly, the pubic symphysis S is determined by designating the most anterior point at the junction of the left and right pelvis bones in the axial 2D images acquired in the standard hip protocol (central 2D images). In another preferred embodiment, the determination of the three pelvis points S, $ASIS_L$ and $ASIS_R$ is performed automatically.

Figure 5A:
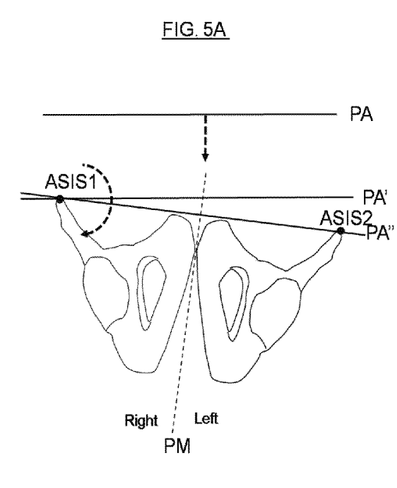
FIG. 5A is a frontal view of the pelvis showing the determination of the anterior superior iliac spines anatomical landmarks.
Figure 5B:
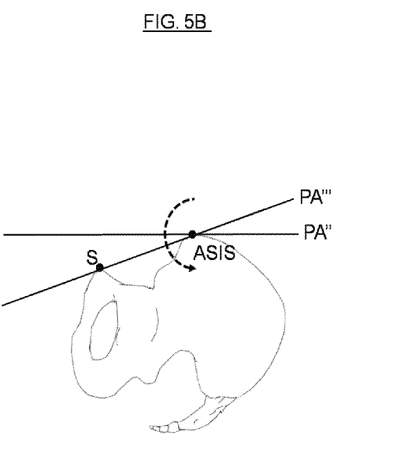
FIG. 5B is a side view of the pelvis showing the determination of the pubic symphysis anatomical landmark

As illustrated in FIG. 5A, a plane PA is first set parallel to the most anterior coronal plane of the 3D image. This plane is translated in the posterior direction until it meets a highest bone point ASIS1 in the highest 2D images, which defines a plane PA'. The plane PA' is then rotated around an axis parallel to the superior-inferior direction of the 3D image, that is perpendicularly to the 2D images used for constructing the 3D image, and passing through the point ASIS1. The rotation is chosen towards the posterior direction, until the plane PA' meets the second highest bone point ASIS2 in the highest 2D images, which defines a plane PA". ASIS1 and ASIS2 determine the pelvis points $ASIS_L$ and $ASIS_R$ labeled according to which side of the mid-sagittal plane PM of the 3D image they are laying in, the pelvis points $ASIS_L$ and $ASIS_R$ defining a pelvis axis ASIS. Finally as illustrated in FIG. 5B, the plane PA" is rotated around the ASIS axis toward the posterior direction until the plane PA" contacts the most anterior bone point of the central 2D images, which determines the pubic symphysis S and defines the plane PA'".

Figure 6:
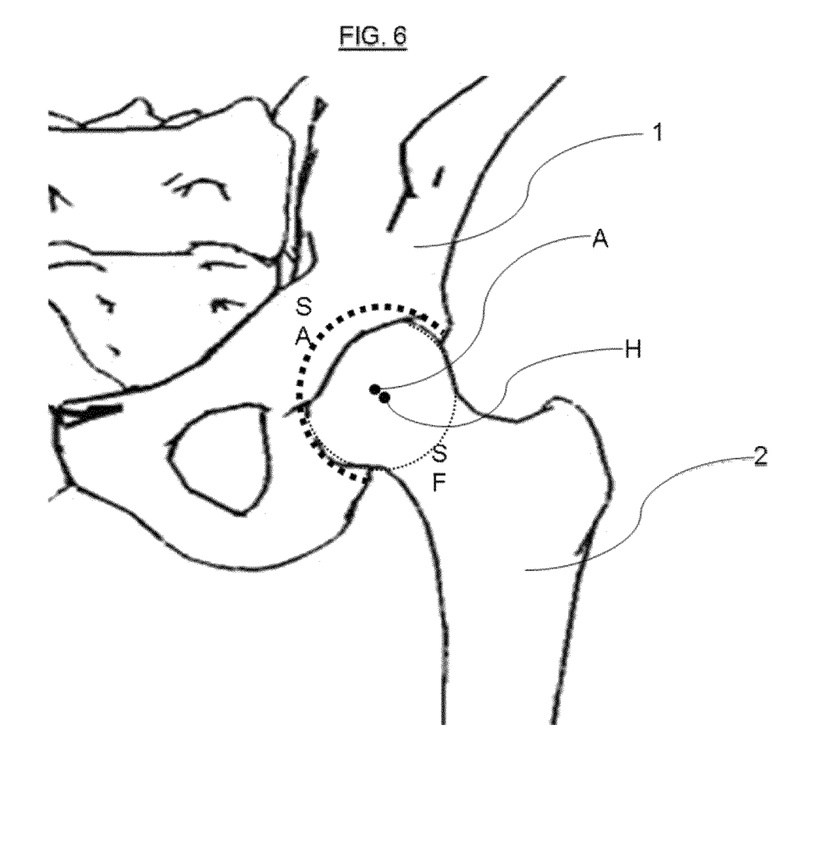
FIG. 6 is zoomed perspective view of the hip joint, illustrating the determination of the acetabulum center.

As illustrated in FIG. 6, on the pelvis bone 1 the acetabulum center point A can be determined similarly as the femoral head center point H of the femur bone 2, using the femoral head center point H as an initial approximation, and applying a dilation to the femoral head sphere SF. From this input, a best-fitting sphere SA of the acetabulum is determined from the acetabulum surface model, using least-square iterative methods.

Figure 7:
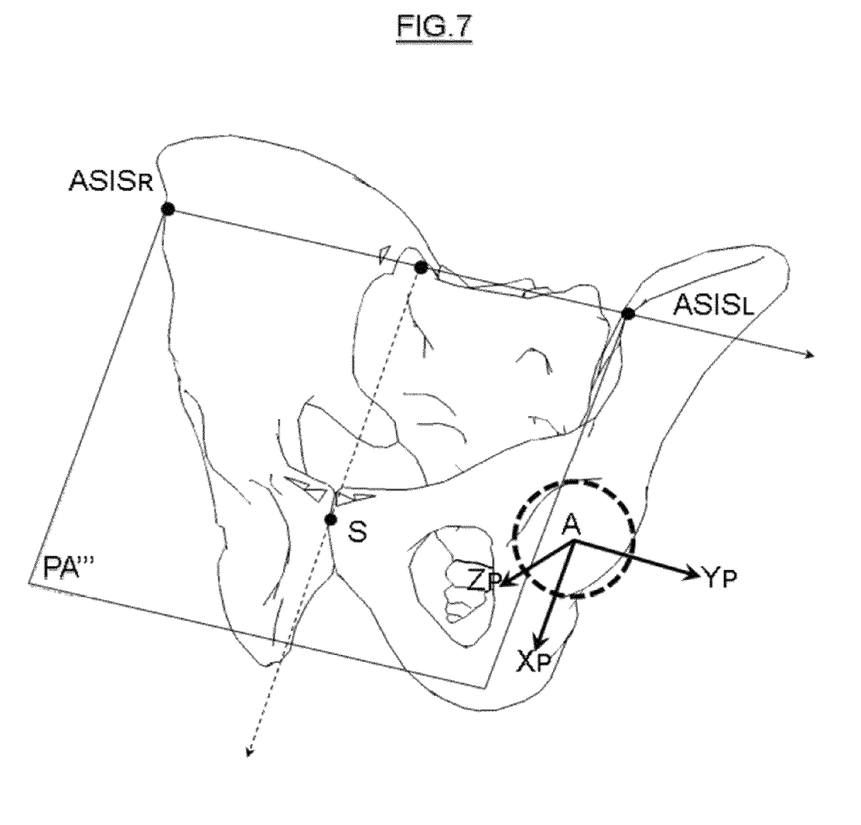
FIG. 7 is a perspective view of a pelvis, showing the 3D coordinate system determined from pelvis anatomical landmarks.

Finally, as illustrated in FIG. 7, from the acetabulum center point A, the pubic symphysis point S and the pelvis ASIS axis, a pelvis coordinate system, defined by an origin and three axes, is determined. The origin of the pelvis coordinate system is centered on the acetabulum center point A, the $Y_P$ axis is defined by the direction of the pelvis axis ASIS, the $X_P$ axis is defined as orthogonal to $Y_P$, in the inferior direction, the $Z_P$ axis is defined as the vector product of $X_P$ by $Y_P$ to build an orthogonal coordinate system. Many other landmarks can be substituted in order to define the pelvis coordinate system, for instance using the tear drops instead of the ASIS, or simply the femoral head centers on both sides instead of the ASIA. It is also possible to use directly the coordinate system of the 3D image that corresponds to the patient lying supine on the 3D imaging examination table. The determination of landmarks defined above can be performed interactively with a mouse or automatically using dedicated algorithms which are not in the scope of this invention.

The next preliminary step is the construction of 3D surface models of the articulated bone surfaces from the 3D image. In the case of CT image, a thresholding process is commonly used to get a 3D surface model. Additional processing using well known mathematical morphology operators is applied to eliminate small connected components and to fill the inside of surfaces so that only external surfaces of the bone remain. However, the surface model is usually not perfect since the thresholding tends to merge the bone surface with adjacent bones and to create some defects in the surface. Therefore, the anatomical landmarks determined above are used to separate the merged 3D surfaces. Applying these methods to the 3D image of the hip will determine a 3D femur surface model and a 3D pelvis surface model. In the case of a damaged hip cartilage, it is possible that the 3D femur surface model and the 3D pelvis surface model are merged at the level of intra-articular zone. The femoral head sphere SF and the acetabulum best-fitting sphere SA are then used to separate the two merged 3D surface models by determining a frontier area. The separation of the 3D surface models can create holes in each of the two 3D surface models. These holes are filled by locally patching the corresponding sphere surface that is the femoral head sphere SF to fill in holes in the femoral head surface of the 3D femur surface model, and the acetabulum best-fitting sphere SA to fill in holes in the acetabulum cup surface of the 3D pelvis surface model.

Figure 8:
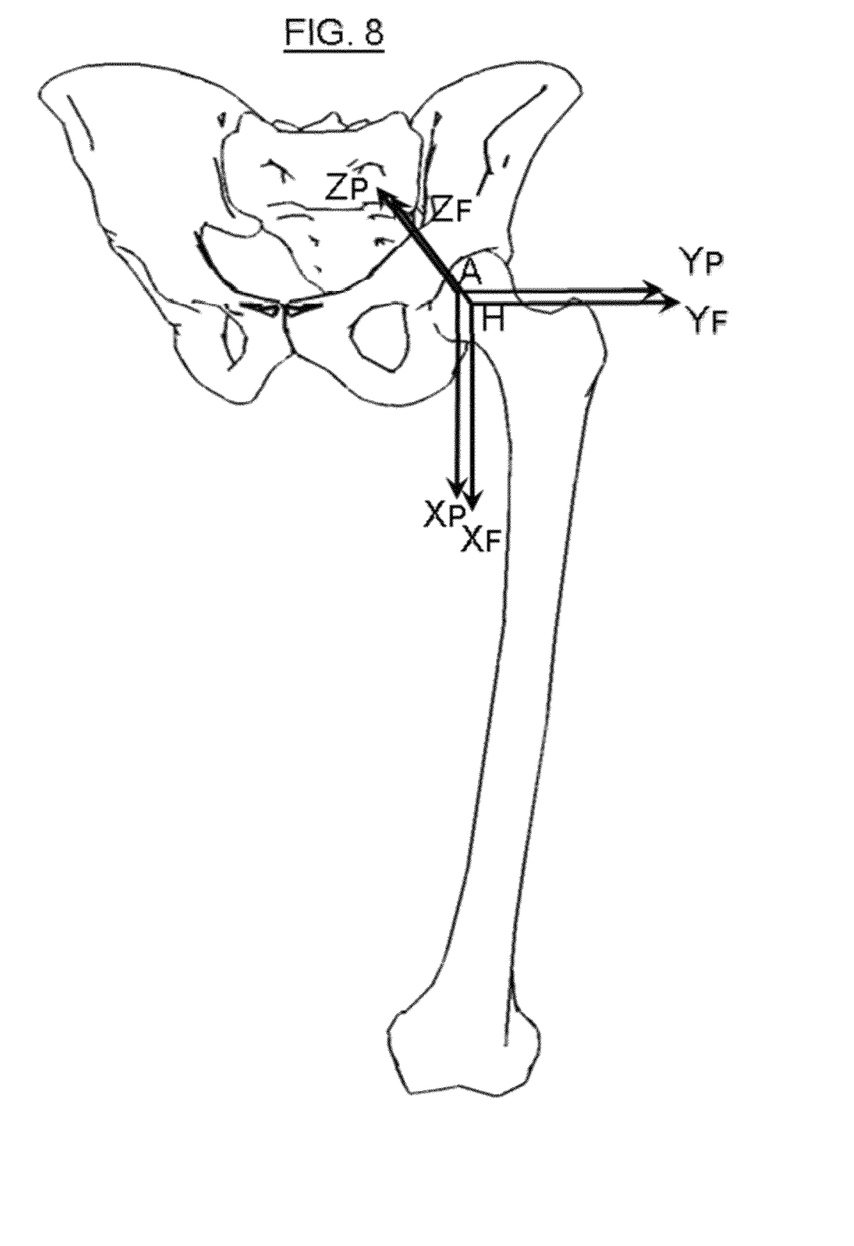
FIG. 8 is a perspective view of the pelvis and the femur illustrating the relationship between the femur coordinate system and the pelvis coordinate system.

The last preliminary step is the determination of the initial position of the femur coordinates system relatively to the pelvis coordinates system. It is possible that there is no exact coincidence of the two coordinates systems origins H and A, as illustrated in FIG. 8. In a preferred embodiment, a read-justed zero position is set for the femur relatively to the pelvis to compensate for a possible pelvis tilt or misaligned leg position during the 3D image examination. In a preferred embodiment, this zero position is determined by aligning the $X_F$ axis of the femur with the $X_P$ axis of the pelvis and the $Y_F$ axis of the femur with the $Y_P$ axis of the pelvis, as well as the origins of the pelvis and femur coordinate systems.

Figure 9:
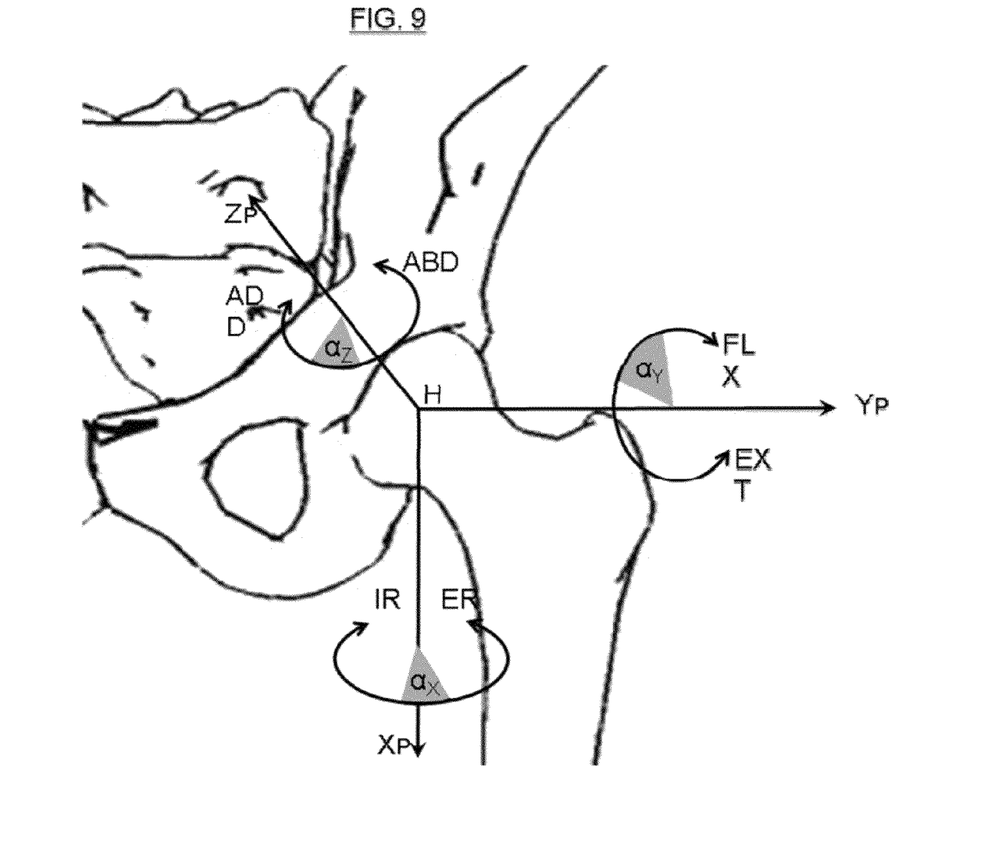
FIG. 9 is a zoomed perspective view of the hip joint, illustrating the axis and direction of the rotations of the femur relatively to the pelvis.

The acetabulum corrected area of the bone overgrowth can now be determined by simulating the movements of rotation of the femur relatively to the pelvis, and by calculating the interpenetration volumes between the two bones during such motion. In a preferred embodiment as shown in FIG. 9, three rotation axes are defined relatively to the axis vectors of the pelvis coordinates system as follows:

[a] a flexion FLX is performed by a rotation around the $Y_P$ vector in the superior direction;
[b] an extension EXT is performed by a rotation around the $Y_P$ vector in the inferior direction;
[c] an angle of flexion extension around $Y_P$ is noted $\alpha_y$;
[d] an abduction ABD is performed by a rotation around the $Z_P$ vector in the lateral direction;
[e] an adduction ADD is performed by a rotation around the $Z_P$ vector the medial direction
[f] an angle of abduction adduction around $Z_P$ is noted $\alpha_z$;
[g] an internal rotation IR is performed by a rotation around the $X_P$ vector in internal direction;
[h] an external rotation ER is performed by a rotation around the $X_P$ vector in the external direction;
[i] an angle of internal external rotation around $X_P$ is noted $\alpha_x$;

The rotations can be represented in many manners such as rotation matrices, quaternions, euler angles, or rotation vectors, and the order of application of the three rotations can be any of the possible combinations. The rotations can be applied around the three vectors of the coordinate system attached to the femur with respect to the pelvis coordinate system, or they can be applied around the three vectors of the coordinate system attached to the pelvis with respect to the femur coordinate system. In a preferred embodiment which is intended to reproduce clinical examination of a hip, a rotation is first applied along the Y axis of the femur, then abduction is applied around the Z axis of the femur, and finally flexion is applied around the X axis of the femur.

When applying combinations of theses rotations, it simulates a ball-and-socket joint in which the femur head center point H is a fixed point. For each combination of rotations, an updated position of the 3D femur surface model relatively to the 3D pelvis surface model is determined. Once the position of the 3D femur surface model has been updated, it is possible to determine if and where the two 3D surface models inter-penetrate. The region of interpenetration between the two bones defines an interpenetration volume that needs to be resected if one wants to regain the amplitude of rotation that has been applied virtually.

The ball-and-socket model for characterizing the articulation is an approximation of the reality. A small residual translation of the femoral head inside the pelvis can also occur during rotations, and several models can be proposed to determine such residual translations. For instance, such residual translations can be calculated such that the minimal distance between the femur and pelvis bone surfaces remain constant along the rotation motions. A brief description of such methods can be found in Puls et al., "Simulation of hip motion for impingement detection: a comparison of four strategies", 16th ESB Congress, Oral Presentations, Tuesday 8 Jul. 2008, Journal of Biomechanics 41(S1). Applying or not the small residual translation does not change the method of the invention. For simplification the description is based on a ball-and-socket joint with no translation.

Figure 10:
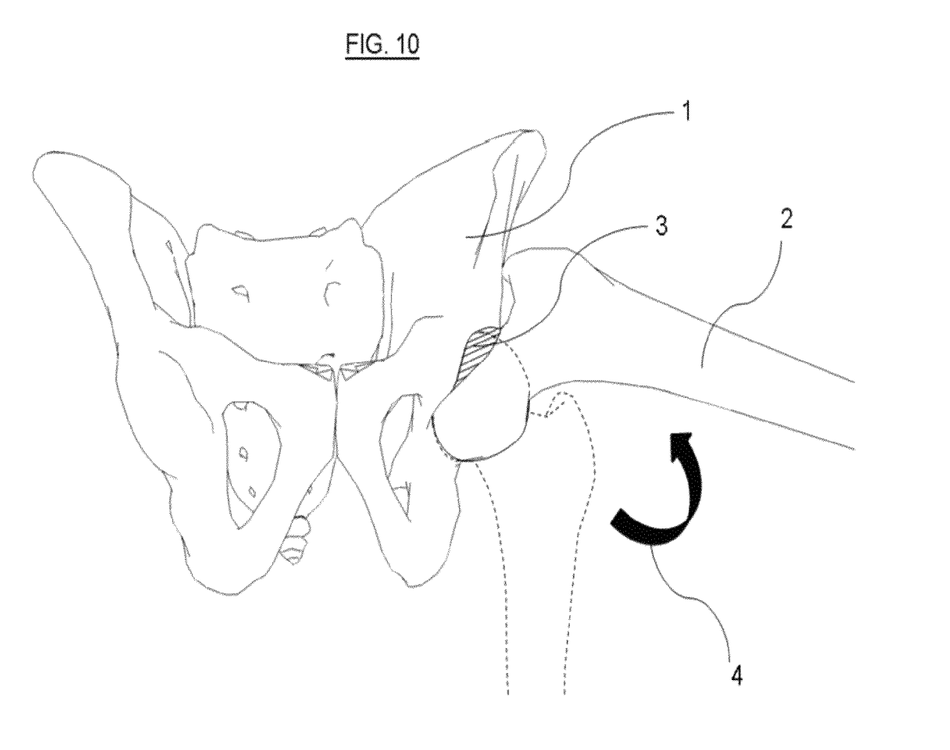
FIG. 10 is a perspective view of the hip joint illustrating an interpenetration area on the pelvis when applying a rotation movement to the femur.

As illustrated in FIG. 10, the corrected area 3 of bone overgrowth is determined by the detection of interpenetration volumes between the 3D pelvis surface model 1 and the 3D femur surface model 2, for a determined set of simulated rotations 4 defined by a triplet AAA=$(\alpha_x, \alpha_y, \alpha_z)$. The rotation 4 is a transform matrix that combines the three rotations around the axis X, Y and Z. In general, the first bone is the pelvis and is assumed to be fixed, whilst the second bone is eth femur and can rotate around the pelvis.

The determined set of simulated rotations to apply to the 3D femur surface model is determined from a patient specific motion pattern. A motion pattern is a set of triplets of angles AAA=$(\alpha_x, \alpha_y, \alpha_z)$, each triplet corresponding to a combination of rotations to be applied to the 3D femur surface model, for a given mathematical representation of rotations. A position of a motion pattern is assimilated to a rotation. More precisely, it is defined as a rotation of the femur coordinate system with respect to the pelvis coordinate system. The triplets set comprises at least a set of extreme positions and optionally a set of intermediate positions required to move from one extreme position to the other. The triplets that constitute a motion pattern generate a set of contiguous motions of one bone relative to the other. In theory, the motion pattern is a continuous trajectory of matrices, but for practical implementation purposes, it is a sampled set of positions with small steps between consecutive positions, like a step of 0.5° for example. A motion pattern is made of one or several parts, that are contiguous or not. For each triplet AAAi along the pattern, the bone surfaces might interpenetrate to define an interpenetration volume Vi. If there is no interpenetration, the interpenetration volume Vi is void. In the invention, a resection volume is calculated as the union of all interpenetration volumes Vi determined along the motion pattern. In theory, the order of positions inside the motion pattern does not affect the final result of the method since the union is a symmetrical operator, but it plays a role in the visualization of motion patterns by the user.

Motion patterns are defined for different types of activities, for which the pathological bone overgrowth limits the amplitude. The simulation of the hip motion according to a predefined motion pattern will determine the regions of bone impingement which should be corrected in order for the patient to regain the full amplitude expected for a given motion pattern.

In a preferred embodiment, the user selects at least one motion pattern from a data base of pre-determined motion patterns. As an example for a dancer, specific motion patterns can be determined in order to describe a frontal or side split. A side split motion can be defined by a full frontal hyper-flexion of one thigh and a full back hyper-extension of the other thigh. For obvious symmetrical reasons, a side split motion pattern can hence be defined by a sequence of successive positions of the femur relatively to the pelvis, in order to describe a full movement of the femur from 90° extension to 90° of flexion. A frontal split motion can be defined by a full frontal opening of both thighs. A frontal split motion pattern can hence be defined by a sequence of successive positions of the femur relatively to the pelvis, in order to describe a full abduction movement of the femur from 0° to 90°. Applying this defined motion pattern to the 3D bone surface models will determine the volumes where there is virtually interpenetration between the 3D femur surface model and the 3D pelvis surface model. As another example for a hockey goal keeper, specific motion patterns can be determined in order to describe a combination of flexion, adduction and internal rotations required to drop down on one's knees when blocking the puck.

Calculating the interpenetration volume between the femur and the pelvis for a given relative position of the motion pattern can be achieved by using various algorithms known in the literature of computer vision, which are applied to the surfaces of the bones modelled by series of contiguous triangular facets. However this usually takes a lot of time for high resolution of the triangular facets, which is important for preserving accuracy. To obtain real-time calculation, in a few milliseconds per position, while maintaining high degree of accuracy, a preferred implementation on a computer uses a volume of voxel elements that fill the inside of each surface bone. A 3D voxel model is therefore associated with each bone; it is made of a regular grid of 3D elements, wherein each 3D element is active if it contains bone and non-active if it does not contain bone. Passing from a surface representation of a bone to a 3D voxel model can be automated, and reciprocally. Using specialized 3D graphics hardware with large memory of at least one gigabytes and specialized software such as CUDA, the interpenetration volume between the first and second bones for a given position of the motion pattern is determined in real-time using the method comprising the following steps:
  a) Apply the position of the motion pattern to transform each voxel element of the second voxel bone model into a transformed voxel element in the coordinate system of the first voxel bone model
  b) Determine the interpenetration volume as the set of active voxel elements of the first voxel bone model that coincide with an active transformed voxel element of the second voxel bone model Such a method can be seen as a realignment of a 3D voxel model which has been rotated towards a reference 3D voxel model.

Using this method, detecting if there is interpenetration and calculating the interpenetration volume can be performed in a few milliseconds on conventional computers equipped with such specialized graphics hardware and software.

In a preferred embodiment the motion pattern can be customized for a specific patient by choosing an initial motion pattern from the motion pattern data base and then adjustments can be applied from user interaction with interactive means such as graphical interface buttons, 2D or 3D mouse, or sliders corresponding to three rotations in both directions. The rotation can be a combination of two or three basis rotations in order to simulate complex hip motions. The user can therefore define target range of motion for several different rotation combinations, based on the patient specific expectations. Each position defined by the user adds to the motion pattern such that interpenetration volumes do cumulate. The user can then record successive rotations movements to simulate a continuous dynamic motion, and thus define a specific motion pattern for a specific patient activity. The adjustment of desired rotations is starting from the initial pattern to accommodate for specific patient characteristics or expectations, for instance having 10° more abduction than the conventional pattern for a hockey player. The motion pattern is a very useful tool since it provides a reference to interactive manipulation. Without using the motion pattern as a basis, interactive simulation performed stand-alone on the three angles of rotations is often very complex, difficult and time-consuming. However, it is important that all motion patterns are defined in a similar coordinate system which is the purpose of the automated determination of femur and pelvis coordinate systems described above. The result of this method is an adjusted motion pattern that is specific to the patient. The motion pattern is also very useful to be stored and applied several times, after changing the shape of one or two bones, and checking if interpenetration volumes do remain or not. The same motion pattern is applied several times for different corrected surfaces of the second bone for selecting an optimal corrected surface of the second bone.

In another embodiment, a motion pattern is defined in several steps, in the following manner:
  [a] Starting from an initial position corresponding to a triplet of rotation angles AAA(0), an initial motion pattern is applied in the direction of a target position to which corresponds a triplet of rotation angles AAA(T), along the trajectory TJ defined by a set of contiguous triplets of angles AAA(1), AAA(2), ... AAA(T). In one example, starting from a position (0°,0°,0°), the trajectory TJ simply consists in incrementing the value of the rotation around the Z axis every half degree: (0°,0°, 0.5°), (0°,0°,1°), (0,0,1.5°), etc.
  [b] For each intermediate position AAA(n) along the trajectory TJ, the computer program tests if there is interpenetration between the two bones or not. The test of interpenetration volume between the two bones is calculated using the method described above with specialized computer graphics The first position on the trajectory TJ where interpenetration is detected is called AAA (I). In the selected example, the first interpenetration occurs at $(0°,0°,\alpha_{zi})$.
  [c] An amount of desired extended motion pattern $\Delta\alpha$ is then selected. This amount is applied in the direction of the trajectory TJ of the pattern at point AAA(I) to generate a new desired position AAA(D)=AAA(I)+$\Delta$A, wherein $\Delta$A is a triplet that characterizes the extent $\Delta\alpha$ in said direction. In the selected example, this amount is simply a desired extent of rotation $\Delta\alpha z$ in order to reach the desired position AAA(D)=(0°,0°, $\alpha_{zi}$+$\Delta$Ez). The interpenetration volume between the two bones is calculated for that particular relative position using the method described above with specialized computer graphics. An updated trajectory is also generated from AAA(I) to AAA(D) and all the intermediate points between AAA(I) and AAA(D) are added to the motion pattern. The resulting interpenetration area calculated on the pelvis bone, or on the femur bone, is the updated interpenetration area. It provides the initial resection volume RV0 that is the output of the method. The resection volume can be also split in two portions, one on the pelvis and one on the femur, with a factor ranging from 0% for full femur resection to 100% for full pelvis resection. For many situations, the process can be stopped at that step.

[d] However, the resection volume RV0 computed on the pelvis might not be smooth and may not lead to a smooth optimal corrected surface. In a preferred embodiment, an additional set of positions is determined in the vicinity of the desired position AAA(D) in the two directions orthogonal to the direction of the trajectory TJ and a with a small range. In the selected example, a set of positions $(\alpha_{xn}, \alpha_{ym}, \alpha_{zi} + \Delta\alpha z)$ is generated where $\alpha_{xn}$ is equal to several values like +/−2.5° and +/−5°, where $\alpha_{ym}$ is equal to several values like +/−2.5° and +/−5°, and all those positions are combined and added to the updated motion pattern to constitute the final motion pattern. For each of those positions of the final motion pattern, the interpenetration volumes are calculated and cumulated together. The union of all such interpenetration volumes is the final resection volume RV1 that is the output of the method. Compared to RV0, RV1 has the advantage that it is smoother, and it captures the possible range of motion around the desired position in a more compliant and robust manner, avoiding that some positions just near the desired position could generate interpenetration.

Figure 11:
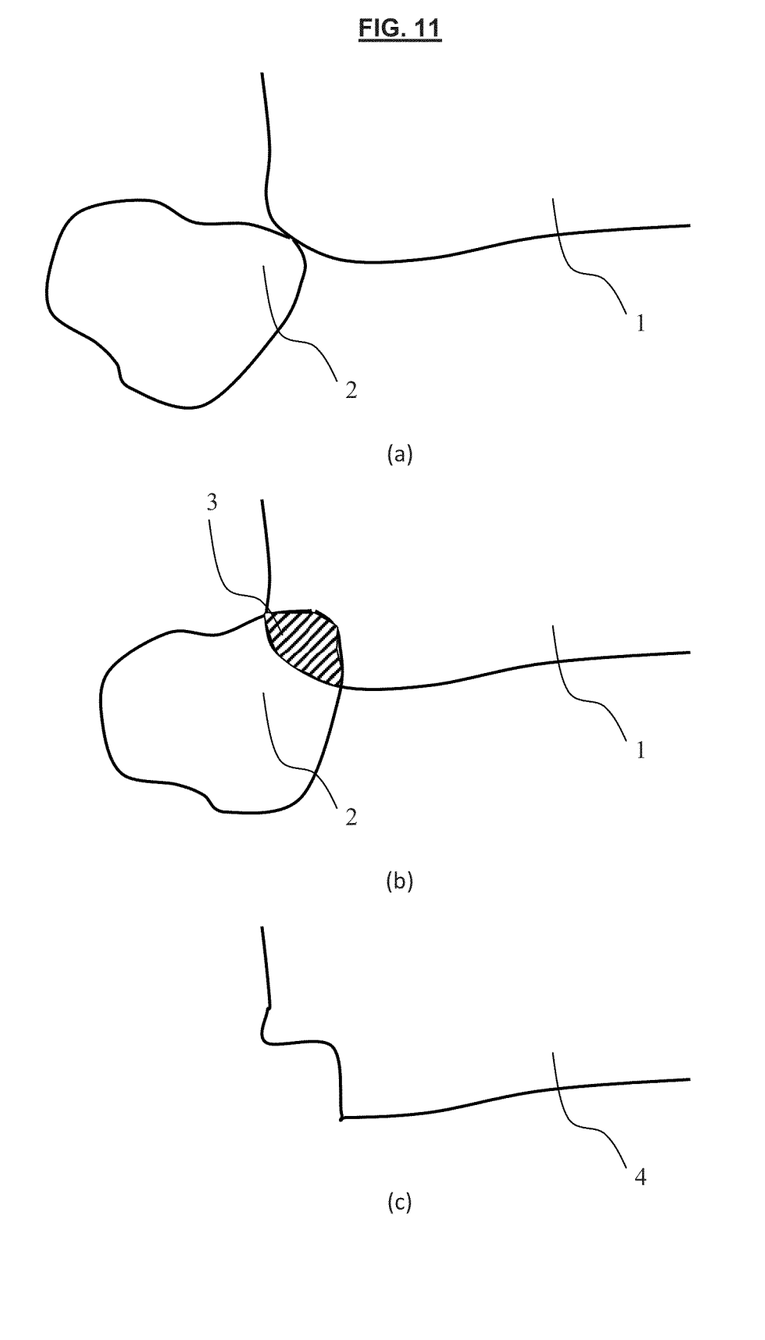
FIG. 11 is a schematic view of the articulation with interpenetration volumes

The method of step (c) described above is illustrated on FIG. 11. FIG. 11(a) represents a schematic 2D slice in the volume, passing by a point where the bone surface voxel 1 is just in contact with the bone voxel model 2. In practice this position corresponds to a situation where there is a very subtle interpenetration of a few tenths of degree. On FIG. 11(b), the bone voxel model 2 has been rotated in the direction of the trajectory TJ and it creates the interpenetration volume 3. On FIG. 11(c), the interpenetration volume generates an optimal corrected surface, resulting in a new shape of the bone surface model 4.

Figure 12:
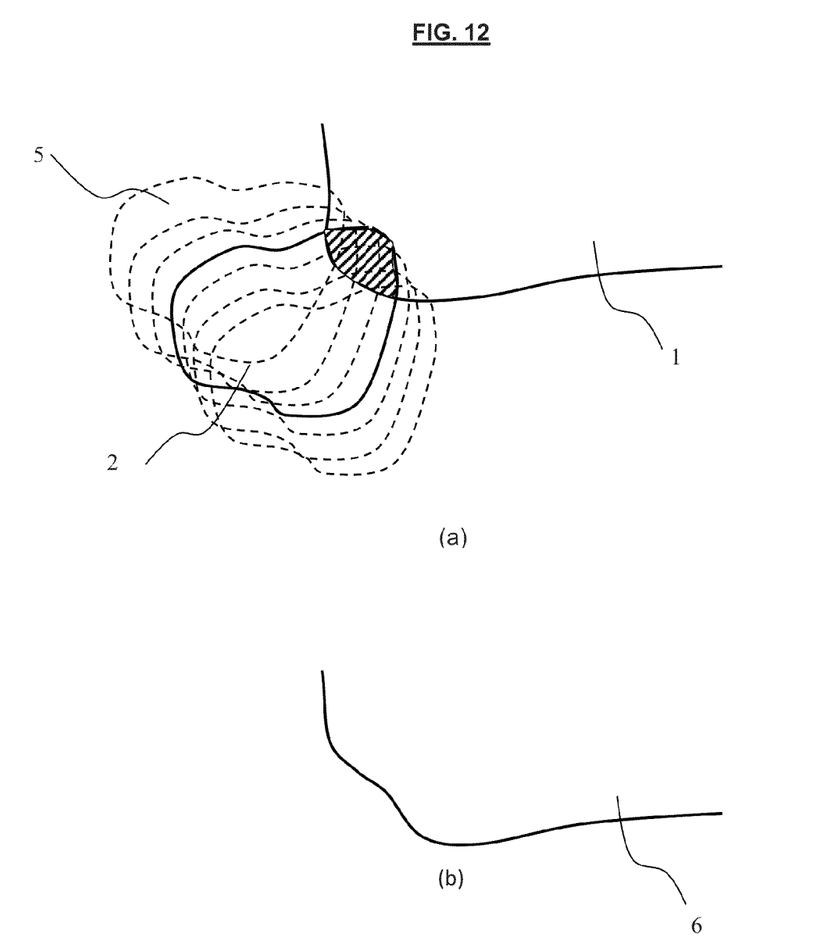
FIG. 12 is another schematic view of the articulation with additional interpenetration volumes

The method of step (d) described above is illustrated on FIG. 12. FIG. 12(a) represents a schematic 2D slice in the volume, similar to FIG. 11(b), wherein several positions 5 of the bone voxel model 2 have been added in the vicinity of the desired position. Each position of the motion pattern generates a new interpenetration volume that cumulates with the previous one. On FIG. 12(b), the union of interpenetration volumes has been calculated to define the resection volume. The latter is removed from the original bone voxel model 2 in order to constitute the final optimal correction surface 6.

In another preferred embodiment, an initial motion pattern can be generated by directly recording the actual motion amplitudes of a patient hip. This step can be performed prior to the surgery, during standard clinical examination of the patient.

In another embodiment, successive positions are collected when applying the specific virtual movements to the hip on the opposite side in order to constitute the motion pattern after a symmetry operator has been applied.

A customized motion pattern can be modified from that basis, for instance to reach extended positions that are necessary for a particular patient, or for creating extended motions around the positions that generate pain. This can be performed by interactive means.

In a preferred embodiment, it is possible to modify the external shape of the femur head-neck junction surface to simulate a bone resection on the femur side. This can be done for example by reshaping the femur external cortical shape on the 3D volume using a drawing tool, or semi-automated tools that reconstruct a smooth shape without bump, and reconstructing a new 3D femur surface model corresponding to a corrected bone. The method of motion patterns, as described above, can then be applied for different simulated resections applied on the femur by using the new updated 3D femur surface. It is thus possible to check if there are still interpenetrations with the 3D pelvis surface model for a given motion pattern before the resection simulated on the femur and to evaluate the impact of such resection on the interpenetration volumes. For that purpose, a motion pattern is constructed using one of the embodiments defined above and it is stored in the computer memory, then several femur resections are attempted, with different parameters, and the motion pattern is read from the computer memory and applied to the pelvis and partially resected femur. The effect of interpenetration can be visualized by coloring in blue the contact areas on the computer display, that simulated methylene blue commonly used to check contacts in dentistry for example. The optimal resection on the femur is then selected. A preferred strategy is to define an anatomical resection on the femur first, to restore a normal shape without bump, and then to apply a selected motion pattern, and finally to perform a virtual resection of the corrected area that corresponds to the interpenetration on the pelvis for that particular pattern. This operation can be repeated for several motion patterns. The user can animate the motion patterns on the computer display, replay them as much as needed, and check that the result matches a desired range of motion and global shapes. Geometric characteristic elements can be computed in addition to constitute values that can be compared from one case to another, such as the new generated CE-angle on the pelvis rim after virtual resection has been applied, wherein the CE-angle is defined in the literature of hip arthroscopy.

The method can be implemented by software running on a standard computer. The user can interact with the software by a standard user interface medium like a mouse, touch screen or the like. Images and graphics are represented on the computer display. At the beginning, the software is used to select and load the 3D image of the specific patient.

In a preferred embodiment, the software is intended to determine the optimal corrected area of a deformed articulation bone surface, which bone presenting a cup shaped structure like the pelvis. In a preferred embodiment, the software is intended to determine the corrected bone surface of bone overgrowth coverage that generates so-called pincer effect.

The description was made with the hip articulation, with the acetabulum of the pelvis in the case of Femoro-Acetabular Impingement (FAI). This description is only illustrative and easily adaptable for other bone articulations of humans or animals with head-neck junction inside a partial cup-like structure.

ADVANTAGES

The invention offers a method for easy, accurate and fast determination of a virtual bone resection of a deformed articular bone surface. The method is based on real-time simulation of the movement of one of the articulated bone relatively to the other and by the detection of interpenetration volumes between the two bones. This dynamic assessment of the articulated bones provides very useful pre-operative information to the surgeon. The bone volume which needs to be resected can therefore be planned and not only partially evaluated at the time of surgery. Moreover, the application of motion patterns to the simulation of the relative movements of the two bones provides the surgeon with a customizable tool to adapt the expected surgical outcomes to each specific patient.

The invention claimed is:

1. A method for real-time determination an optimal corrected surface of a first bone and/or a second bone forming together an articulation, the first and/or second bones presenting an overgrowth deformation, said corrected surface providing a greater range of motion of the articulation, the method comprising the following steps:
  i) constructing from acquired images of the articulation 3D voxel models of the first bone and the second bone;
  ii) for each of first and second bone voxel models, constructing a coordinate system defined by a center and three axes;
  iii) applying a motion pattern on the coordinate system of the second bone with respect to the coordinate system of the first bone, a motion pattern being a set of contiguous positions of the first or second bone coordinate systems with respect to the other bone coordinate system, the contiguous positions defining a movement of one bone with respect to the other, wherein said motion pattern is initially loaded from a data base of predefined motion patterns;
  iv) determining a resection volume from said motion pattern as being the union of interpenetration volumes of the first or second bone voxel model with the other bone voxel model for each position of the motion pattern;
  v) determining the optimal corrected surface by virtually removing said resection volume from the first and/or the second bone voxel model.

2. The method of claim 1, wherein said motion pattern defines a movement of the second bone voxel model with respect to the first bone voxel model, the first bone voxel model being fixed, each position of the second bone voxel model during the movement being defined by three angles of rotation around the axes of the coordinate system of the first bone.

3. The method of claim 1, wherein said motion pattern defines a movement of the first bone voxel model with respect to the second bone voxel model, the second bone voxel model being fixed, each position being defined by three angles of rotation around the axes of the coordinate system of the first or second bone.

4. The method of claim 1, wherein each motion pattern of said data base represents the movement and amplitudes of the articulation corresponding to a specific activity.

5. The method of claim 1, wherein the articulation is a hip, the first bone is the pelvis presenting an acetabulum rim, and the second bone is the femur, the bone overgrowth being located on the acetabulum rim and/or on the femur.

6. The method of claim 1, wherein the articulation is modeled as a ball-and-socket joint.

7. The method of claim 1, wherein the articulation is modeled as a ball-and-socket joint with additional residual translations.

8. The method of claim 1, wherein said resection volume is split into a resection volume of the first bone and a resection volume of the second bone.

9. The method of claim 1, wherein said motion pattern is updated according to the following steps:
  a. Select an initial motion pattern in the data base of motion patterns;
  b. Apply said initial motion pattern to the second bone voxel model and detect the first position that generates interpenetration between the first and the second bone voxel models;
  c. Extend the motion pattern in a given direction from said first position to determine a trajectory that reaches a desired position, and add positions of the trajectory to the updated motion pattern, including at least the desired position.

10. The method of claim 9, wherein said direction is generated manually by the user with interactive means.

11. The method of claim 9, wherein said direction is generated automatically as the continuation of the trajectory corresponding to the initial pattern.

12. The method of claim 1, further comprising a step of generating new positions in the vicinity of said desired position and adding them to the updated motion pattern to generate the final motion pattern.

13. The method of claim 12, wherein said vicinity is determined as a set of additional positions starting from the desired position and going in the two directions orthogonal to the direction of the trajectory of the motion pattern with small ranges.

14. The method of claim 1, wherein the same motion pattern is applied several times for different corrected surfaces of the second bone for selecting an optimal corrected surface of the second bone.

15. The method of claim 1, wherein a computer with specialized hardware and software is used to determine said interpenetration volume between the first and second bones for a given position of the motion pattern, the method comprising the following steps:
  a. Apply the position of the motion pattern to transform each voxel element of the second voxel bone model into a transformed voxel element in the coordinate system of the first voxel bone model;
  b. Determine the interpenetration volume as the set of active voxel elements of the first voxel bone model that coincide with an active transformed voxel element of the second voxel bone model.

* * * * *